United States Patent [19]
Marcus et al.

[11] Patent Number: 5,854,248
[45] Date of Patent: *Dec. 29, 1998

[54] NEFAZODONE: USE IN MIGRAINE PROPHYLAXIS

[75] Inventors: Ronald N. Marcus; Neil M. Sussman, both of Hamden, Conn.

[73] Assignee: Bristol-Myers Squibb Company, Princeton, N.J.

[*] Notice: This patent issued on a continued prosecution application filed under 37 CFR 1.53(d), and is subject to the twenty year patent term provisions of 35 U.S.C. 154(a)(2).

[21] Appl. No.: 843,671

[22] Filed: Apr. 10, 1997

Related U.S. Application Data

[60] Provisional application No. 60/022,836 Jul. 31, 1996.

[51] Int. Cl.$^6$ .................................................. A61K 31/495
[52] U.S. Cl. ............................................................ 514/255
[58] Field of Search ............................................. 514/255

[56] References Cited

U.S. PATENT DOCUMENTS

| | | | |
|---|---|---|---|
| 4,338,317 | 7/1982 | Temple et al. | 424/250 |
| 5,116,852 | 5/1992 | Gammans | 514/359 |

OTHER PUBLICATIONS

Chemical Abstracts, vol. 116, No. 17, Potentiation of opioid analgesia by the antidepressant nefazodone. Apr. 1992. Abrstract No. 166183a. Pick et al. page 62. *Eur. J. Pharmacol.*, 211(3), 375–381.

USP Dictionary of USAN and International Drug Names, 1995, p. 459.

D.P. Taylor, et al, "Nefazodone Hydrochloride," *Drugs of the Future*, 12(8), pp. 758–759 (1987).

A. Eison, et al, "Nefazodone: Preclinical Pharmacology of a New Antidepressant," *Psychopharmacology Bulletin*, 26(3), pp. 311,315 (1990).

Nappi, et al., *Headache*, 30, 1990: pp. 438–444.
Foster, et al., *Headache*, 34, 1994: pp. 587–589.
Silberstein, et al., and Spierings, *Headache*, 32, 1992: pp. 242–244.
Workman, et al., *Am. J. Psychiatry*, 149:5, 1992: pp. 712–713.

*Primary Examiner*—Phyllis Spivack
*Attorney, Agent, or Firm*—Richard P. Ryan

[57] ABSTRACT

Nefazodone and its pharmaceutically acceptable salts are useful in prophylactic treatment of recurrent headache disorders, as, in particular, vascular and migraine headaches.

7 Claims, No Drawings

NEFAZODONE: USE IN MIGRAINE PROPHYLAXIS

FIELD OF INVENTION

This invention relates to the prophylactic treatment of vascular headaches, especially migraine, with nefazodone.

BACKGROUND OF THE INVENTION

This application claims the benefit of U.S. provisional application 60/022,836 filed Jul. 31, 1996.

This invention is concerned with a drug bio-affecting body-treating process which employs the compound 2-[3-[4-(3-chlorophenyl)-1-piperazinyl]propyl]-5-ethyl-2,4-dihydro-4-(2-phenoxyethyl)-3H-1,2,4-triazol-3-one or a pharmaceutically acceptable acid addition salt thereof.

This compound has the following structural formula (I)

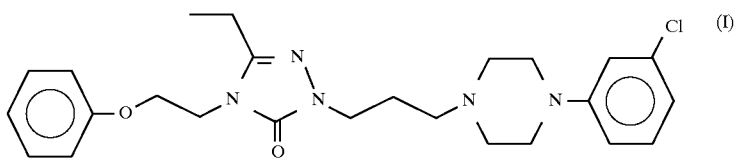

and is known as nefazodone. The hydrochloride salt has been referred to in the literature as MJ 13754-1 and as BMY 13754, as well as nefazodone hydrochloride, which is the United States Adopted Name (USAN); refer to "USP Dictionary of USAN and International Drug Names," 1995, p. 459.

Synthesis of nefazodone and close analogs and disclosure of its pharmacology are described in the following patents and publications.

1. Temple, et al, U.S. Pat. No. 4,338,317 issued Jul. 6, 1982.
2. Gammans, U.S. Pat. No. 5,116,852, issued May 26, 1992.
3. D. P. Taylor, et al, "Nefazodone Hydrochloride," *Drugs of the Future*, 12(8) pp. 758–759 (1987).
4. A. Eison, et al, "Nefazodone: Preclinical Pharmacology of a New Antidepressant," *Psychopharmacology Bulletin*, 26(3) pp. 311,315 (1990).

Clinical studies of nefazodone have indicated its usefulness as an antidepressant agent and nefazodone hydrochloride has been approved by the U.S. Food and Drug Administration for use in treating depressed patients. Nefazodone also appears to have sleep normalizing properties in a human population. This contrasts with effects on sleep seen for other antidepressant drugs.

The method of the present invention can be distinguished from the above prior art in that it is directed to a distinct patient population characterized by a disease state different from that related to depression disclosed in this prior art.

For patients suffering from recurrent vascular headaches such as migraine, cluster, or chronic daily headaches, three treatment considerations are important.

1. No single therapy is effective in all patients with the same type of headache.
2. Prophylaxis is valuable in chronic muscle-contraction, migraine and cluster headaches.
3. Drug dependence potential should be taken into account in selection of a prophylactic headache medication.

Agents that have found some use in prophylactic headache therapy comprise ergot alkaloids, beta-blocking agents, calcium-channel blocking agents, non-steroidal antiinflammatory drugs, methysergide (a serotonin antagonist), divalproex sodium (Depakote, an antiepilepsy agent), and antidepressants. With antidepressant agents, the relationship between depression and chronic headache is not known but some antidepressant drugs have been reported to be effective in the treatment of migraine and chronic headache disorders.

Nappi, et al. in *Headache*, 30:438–444, 1990, reported a comparative treatment study in patients with chronic headache as well as depression. Both ritanserin and amitriptyline appeared to be effective in treating this patient population although the antimigraine response was reported to be relatively independent of the antidepressant activity.

Foster, et al. in *Headache*, 34:587–589, 1994, reported that paroxetine appeared to be effective in the treatment of chronic daily headache. Co-existing depression was not an entry criterion and was not evaluated in this study population. Amitriptyline, a tricyclic antidepressant, has been reported to be effective in non-depressed patients with severe migraine and in depressed patients with less severe migraine.

While the use of nefazodone for prophylactic treatment of recurrent headache is novel, other antidepressant agents have been disclosed as being used in the prophylactic treatment of headache disorders. There is, however, no direct connection between headache prophylaxis activity and antidepressant activity, as some potent antidepressants have not been shown to have prophylactic headache activity. The differences in the comparative efficacy of agents that act at different points in the serotonin system may be attributed to the pathophysiology of recurring headaches. It is possible that nefazodone possesses important clinical distinctions from other available treatments, because of its dual effects on serotonergic transmission (i.e., 5-HT$_2$ antagonism and 5-HT uptake inhibition) and norepinephrine uptake.

The most relevant antidepressant drug for comparison to nefazodone would seem to be trazodone, with its structure (II) containing a meta-chlorophenylpiperazine moiety

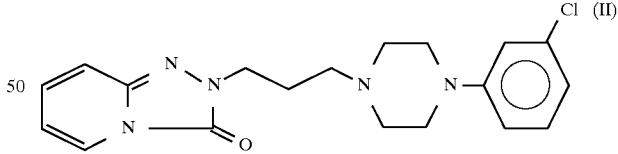

similar to nefazodone.

Meta-chlorophenylpiperazine (MCPP) itself has been reported to be an initiator of migraine (see e.g. Silberstein, et al. and Spierings in *Headache*, 32:242–244, 1992). Trazodone has been reported to induce migraine attack, presumably via release of MCPP (see Workman, et al., *Am. J. Psychiatry*, 14 9/5:712–713, 1992).

We believe that upon consideration of all applicable prior art there is no teaching or suggestion that nefazodone would be useful in the prophylactic treatment of recurrent headache disorders.

SUMMARY OF THE INVENTION

The process of the present invention is intended for the prophylactic treatment of recurrent headache disorders of which vascular headache, such as migraine and cluster; and chronic daily headache are specific headaches to be treated. The process essentially involves administration of nefazodone, or a pharmaceutically acceptable acid addition salt thereof, to one in need of such treatment. For use in the instant process, oral administration of nefazodone hydrochloride ranges from about 100 to 600 mg per day. Administration of about 200 to 500 mg per day in divided doses is anticipated as being the preferred dosage regimen. While various treatments have been employed for headache prophylaxis, it is possible that nefazodone possesses important clinical distinctions from other available treatments because of its dual effects on serotonergic transmission and norepinephrine uptake.

DETAILED DESCRIPTION OF THE INVENTION

Chronic recurrent headaches, particularly those of the vascular category, usually lead to patient consultation with a physician because of frequency and pain intensity which is often incapacitating. Although there is no universally accepted classification system for headache, recurrent headache disorders, for purposes of the present invention, refers mainly to vascular headaches, such as migraine and cluster headaches, and to chronic daily headache whether vascular, muscle tension, or vascular-muscle in nature. It is an object of the present invention to treat all recurrent headache disorders by prophylactic administration of an effective amount of nefazodone or one of its pharmaceutically acceptable salts or hydrates.

While various prophylactic treatments have been employed in patients suffering from recurrent headache disorders, clinical results in general appear to be variable and, for many agents, undesirable side-effects limit their use. It is, therefore, a further objective of the present invention to provide a method of prophylactic treatment that minimizes undesirable side-effects. To that end, nefazodone is relatively free of adverse effects, particularly lacking adverse effects with respect to sleep and sexual responsiveness.

It has now been clinically observed that prophylactic administration of nefazodone alleviates the frequency and/or intensity of recurrent headache disorders.

In a study of approximately 20 patients suffering from recurring vascular headaches who either did not tolerate or were unresponsive to tricyclic antidepressants or selective serotonin reuptake inhibitors, nefazodone therapy was initiated. Improvement across the group was observed with respect to both frequency of headaches and level of tolerance of the headaches. In addition, nefazodone was well tolerated by the patient group.

In another study, seven patients suffering from chronic daily headaches of the mixed migraine/tension-type headache disorder were treated with nefazodone. The patients were given nefazodone in the range of 150–250 mg once a day or a divided 300 mg dose twice a day. Clinical experience with patients afflicted with chronic daily headaches has led to a commonly held opinion that any improvement at all in this patient population is a major achievement. Nefazodone treatment resulted in decreases in pain severity and/or headache frequency. Also indicative of nefazodone's headache prophylaxis was a decrease in concomitant pain reliever use by the study population while being given nefazodone.

Currently, studies are being planned to continue the evaluation of nefazodone's utility in the prophylactic treatment of recurrent headache disorders.

The method of the present invention essentially involves administration of nefazodone, or a pharmaceutically acceptable acid addition salt thereof, to a patient in need of such treatment. Pharmaceutically acceptable acid addition salts of nefazodone and methods of pharmaceutical formulation are described in the patent of Temple, et al, U.S. Pat. No. 4,338,317, which is incorporated herein in its entirety by reference.

Administration of nefazodone hydrochloride according to the present invention may be by the parenteral, oral, or rectal routes. The oral route is preferred, however. The clinical dosage for alleviation of headache disorders is expected to be around 300 mg per day, generally in the 200 to 600 mg range and preferably in the range of 200 to 500 mg per day. Since the dosage should be tailored to the individual patient, the usual practice is to commence with a dose of about 50 mg administered once or twice a day and then to increase the dose every week by 50 to 100 mg at each dosage time until the desired response is observed or until the patient exhibits side effects.

We claim:

1. A method for prophylactic treatment of recurrent headache disorders which comprises administering a non-toxic therapeutically effective dose of nefazodone or a pharmaceutically acceptable acid addition salt thereof to a patient in need of such treatment.

2. The method of claim 1 wherein nefazodone hydrochloride is employed and dosage is by the oral route.

3. The method of claim 1 wherein vascular headache is the specific recurrent headache disorder afflicting said patient.

4. The method of claim 3 wherein migraine headache is the specific vascular headache afflicting said patient.

5. The method of claim 1 wherein chronic daily headache is the specific recurrent headache disorder afflicting said patient.

6. The method of claim 2, 3, 4, or 5 wherein said patient is an adult and a daily dose of from about 100 mg to 600 mg is employed.

7. The method of claim 6 wherein said daily dose is divided and administered b.i.d.

* * * * *